United States Patent
Geromanos et al.

(10) Patent No.: US 8,271,207 B2
(45) Date of Patent: Sep. 18, 2012

(54) SYSTEM AND METHOD FOR ABSOLUTE QUANTITATION OF PROTEINS USING LC/MS

(75) Inventors: Scott Geromanos, Middletown, NJ (US); Jeffrey Cruz Silva, Beverly, MA (US); Hans Vissers, Huizen (NL); Guo-Zhong Li, Westborough, MA (US)

(73) Assignee: Waters Technologies Corporation, Milford, MA (US)

( * ) Notice: Subject to any disclaimer, the term of this patent is extended or adjusted under 35 U.S.C. 154(b) by 903 days.

(21) Appl. No.: 11/914,578

(22) PCT Filed: Jun. 2, 2006

(86) PCT No.: PCT/US2006/021517
§ 371 (c)(1),
(2), (4) Date: Aug. 1, 2008

(87) PCT Pub. No.: WO2006/132994
PCT Pub. Date: Dec. 14, 2006

(65) Prior Publication Data
US 2009/0306901 A1    Dec. 10, 2009

Related U.S. Application Data

(60) Provisional application No. 60/686,967, filed on Jun. 3, 2005.

(51) Int. Cl.
*G01N 30/04*     (2006.01)
*G01N 30/00*     (2006.01)
*G01N 30/26*     (2006.01)
*G01N 30/72*     (2006.01)

(52) U.S. Cl. .............. 702/23; 702/19; 702/27; 702/28
(58) Field of Classification Search ............ 702/19, 702/23, 27, 28, 85, 179, 182, 183; 250/281; 435/23; 436/173
See application file for complete search history.

(56) References Cited

U.S. PATENT DOCUMENTS

| | | | |
|---|---|---|---|
| 7,422,865 B2 * | 9/2008 | Fischer | 435/23 |
| 7,473,892 B2 * | 1/2009 | Sano et al. | 250/281 |
| 7,632,685 B2 * | 12/2009 | Ivey et al. | 436/173 |

(Continued)

FOREIGN PATENT DOCUMENTS

JP    2001357313 A    12/2001

OTHER PUBLICATIONS

Hughes et al, Quantitative Proteomic Analysis of Drug-Induced Changes in Mycobacteria, Journal of Proteome Research, 2006, pp. 54-63, vol. 5, No. 1, American Chemical Society.

(Continued)

*Primary Examiner* — Michael Nghiem
*Assistant Examiner* — Felix Suarez
(74) *Attorney, Agent, or Firm* — Muirhead & Saturnelli, LLC

(57) ABSTRACT

Absolute quantitation of protein in a sample is provided by comparing a sum or average of the N highest ionization intensities observed for peptides of a particular protein along with a calibration standard. The calibration standard can be in the form of a table generated by prior protein peptide analysis performed using one or more pre-determined proteins. The comparison is used to determine a corresponding absolute quantity of protein based on the observed sum or average of ionization intensities. A simple conversion factor can be applied to the calibration standard value to determine the absolute quantity of protein in the sample.

20 Claims, 13 Drawing Sheets

U.S. PATENT DOCUMENTS

| | | | |
|---|---|---|---|
| 7,645,613 B2 * | 1/2010 | Ivey et al. | 436/173 |
| 2003/0113797 A1 | 6/2003 | Jia et al. | |
| 2004/0229283 A1 | 11/2004 | Gygi et al. | |
| 2005/0095611 A1 | 5/2005 | Chan et al. | |

OTHER PUBLICATIONS

Gerber et al, Direct Profiling of Multiple Enzyme Activities in Human Cell Lysates by Affinity Chromatography / Electrospray Ionization Mass Spectrometry: Application to Clinical Enzymology, Analytical Chemistry, 2001, pp. 1651-1657, vol. 73, No. 8, American Chemical Society.

Silva et al, Quantitative Proteomic Analysis by Accurate Mass Retention Time Pairs, Analytical Chemistry, 2005, pp. 2187-2200, vol. 77, No. 7, American Chemical Society.

\* cited by examiner

| pmol | gp | | | bs | | | adh | | | eno | | | hb | | | ha | | |
|---|---|---|---|---|---|---|---|---|---|---|---|---|---|---|---|---|---|---|
| 5.00 | 298 | 313 | 298 | 268 | 421 | 328 | 286 | 545 | 271 | 413 | 572 | 416 | 119 | 206 | 104 | 148 | 165 | 123 |
| 2.00 | 124 | 118 | 110 | 167 | 116 | 92 | 203 | 112 | 108 | 223 | 169 | 161 | 67 | 45 | 53 | 76 | 42 | 50 |
| 1.00 | 62 | 62 | 60 | 94 | 61 | 47 | 107 | 50 | 58 | 118 | 86 | 68 | 40 | 32 | 22 | 24 | 16 | 19 |
| 0.50 | 28 | 27 | 24 | 45 | 28 | 26 | 52 | 28 | 21 | 51 | 54 | 43 | 17 | 13 | 8 | 28 | 18 | 9 |
| 0.25 | 12 | 13 | 9 | 14 | 12 | 6 | 24 | 11 | 6 | 26 | 26 | 8 | 7 | 18 | 5 | 7 | 2 | 7 |
| 0.10 | 7 | 3 | 3 | 5 | 6 | 3 | 3 | 10 | | 6 | 5 | 5 | | | | | | |

Response values of top three ionizing peptides (*1000) — 1600

Figure 16

| | Sum Response Values | | | | | | |
|---|---|---|---|---|---|---|---|
| pmol | gp | bs | adh | eno | hab | Avg | Cv |
| 5.00 | 909 | 1017 | 1102 | 981 | 865 | 974.8 | 10 |
| 2.00 | 352 | 375 | 423 | 387 | 333 | 374 | 9 |
| 1.00 | 184 | 202 | 215 | 190 | 153 | 188.8 | 12 |
| 0.50 | 79 | 99 | 101 | 104 | 93 | 95.2 | 10 |
| 0.25 | 34 | 32 | 41 | 42 | 46 | 39 | 15 |
| 0.10 | 13 | 14 | | 11 | | 12.7 | |

| | Average Response Values | | | | | | |
|---|---|---|---|---|---|---|---|
| pmol | gp | bs | adh | eno | hab | Avg | Cv |
| 5.00 | 303 | 339 | 367 | 327 | 288 | 324.8 | 10 |
| 2.00 | 117 | 125 | 141 | 129 | 111 | 124.6 | 9 |
| 1.00 | 61 | 67 | 72 | 63 | 51 | 62.8 | 12 |
| 0.50 | 26 | 33 | 34 | 35 | 31 | 31.8 | 10 |
| 0.25 | 11 | 11 | 14 | 14 | 15 | 13 | 15 |
| 0.10 | 4 | 5 | 7 | 4 | | 5 | |

SYSTEM AND METHOD FOR ABSOLUTE QUANTITATION OF PROTEINS USING LC/MS

The present application claims the benefit of U.S. Provisional Application No. 60/686,967, filed Jun. 3, 2005, which is hereby incorporation by reference in its entirety.

BACKGROUND

1. Field of the Invention

The present invention relates generally to LC/MS analysis of protein mixtures. More specifically, the present invention relates to absolute quantitation of proteins by LC/MS analysis of enzymatically digested proteins in simple or complex mixtures.

2. Background of the Invention

The study of proteins is crucial in a number fields including understanding and combating disease through identification of proteins, discovering disease biomarkers, studying protein involvement in specific metabolic pathways and identifying protein targets in drug discovery. An important technique that is often used in these studies is liquid chromatography combined with electrospray ionization mass spectrometry (ESI-LC/MS) to quantitate and identify peptides and proteins present in simple and complex mixtures.

One approach for quantifying peptides and proteins in simple and complex mixtures involves determining the corresponding relative abundance between two experimental conditions. During these experiments it is important to compare identical components between the two experiments in order to accurately determine relative ratios of peptides to particular protein(s). By doing so, multiple relative abundance values for each peptide to a given protein can be obtained to quantitatively characterize the differential expression of proteins between and among different physiological conditions.

Another approach to the quantitative study of proteins is to determine the absolute concentration of the peptides and/or proteins that result from enzymatic digestion of a given protein sample. In this approach, digestion of a protein sample using a protease such as trypsin produces many smaller polypeptides, each having a specific primary amino acid sequence. It is known that a given mole quantity of protein produces the same mole quantity for each tryptic peptide cleavage product if the proteolytic digest is allowed to proceed to completion. Thus, determining the mole quantity of tryptic peptide to a given protein allows determination of the mole quantity of the originating protein in the sample. Absolute quantitation of the protein can then be accomplished by determining the absolute quantity of the peptides to that protein(s) in the digest mixture.

Typically, absolute quantitation of proteins requires one or more external reference peptides that are used to generate a calibration response curve for specific polypeptides from a given protein (i.e., synthetic tryptic polypeptide product). The absolute quantitation of the given protein is determined from the observed signal response for the specific polypeptide in the sample relative to that generated in the calibration curve. If the absolute quantitation of a number of different proteins is to be determined, separate calibration curves are generated for each specific external reference peptide for each protein.

U.S. Patent Application No. 2004/0229283 to Gygi et al. ("Gygi") describes a conventional technique for absolute quantitation of proteins in complex mixtures that uses a synthesized derivative peptide as a standard. A derivative peptide is a peptide that is chemically identical to a naturally occurring peptide of a given protein. The derivative peptide is introduced to a complex mixture. The mixture is analyzed using LC/MS resulting in ionization intensities for the derivative peptide. This intensity signal response is compared with an intensity calibration curve created using the introduced synthetic molecule to determine the amount of the derivative protein in the mixture. A disadvantage with using synthetic peptides is that extra steps are required to synthesize an authentic sample, and to later "spike" the synthetic standard prior to being able to determine the absolute quantity of the protein itself.

Another technique for absolute quantitation of proteins employs an S35-methionine or other types of radio label, whose specific activity is known. In this radio labeling techniques, an amino acid, such as S35-methionine, that is radio labeled is fed to a cell. As proteins are synthesized, the proteins incorporate the S35-methionine instead of methionine. Based on the extent of incorporation of the radio label, the absolute amount of the peptide or protein can be determined. A disadvantage with using radio labels is that in some instances, such as studies on humans or other organisms, radioactive feeding or doping is expensive and may be deleterious to the subject and therefore impractical. Consequently, determining absolute quantitation of proteins using radio label techniques is limited to expendable biological systems such as microbes and plants.

Other protein quantitation techniques provide relative quantitation of protein amounts between two samples. Relative quantitation provides information as to how specific protein abundances change due to a perturbation (environment-induced, drug-induced, disease-induced). But, such relative quantitation techniques do not provide the absolute quantity of a particular protein present in a sample.

Consequently, a technique for determining the absolute quantity of a protein in a sample that does not suffer from the disadvantages or requirements of the prior art is required.

BRIEF SUMMARY OF THE INVENTION

Embodiments of the present invention provide absolute quantitation of proteins from LC/MS data of simple or complex mixtures of chemically- or enzymatically-generated peptides without requiring synthesis of external reference peptide(s) or the implementation of radio labeling methods. Embodiments of the present invention use a single calibration standard that is applicable to the subsequent absolute quantitation of all other proteins.

In an embodiment of the present invention, one or more predetermined calibration standard proteins are chemically or enzymatically degraded to their corresponding polypeptide cleavage products. The resulting polypeptide products are analyzed by LC/MS. A calibration standard table of the average signal response of the top N most efficiently ionizing peptides associated with one or more predetermined calibration standard proteins is created as a function of known quantity (moles). During an actual experiment, proteins in a mixture are degraded chemically or enzymatically into their corresponding polypeptide cleavage products and the resulting polypeptide products are analyzed by LC/MS. For each protein present, the top N most intense polypeptides are selected and their corresponding intensities are averaged. The average signal response value from the top N most efficiently ionizing polypeptides of a given protein in the sample is compared to the average signal response values annotated in the calibration standard table to determine the absolute quantity of each protein present. A conversion factor or interpolation technique can be used to determine the absolute quantity of a protein(s) present when the average signal response value is not in the calibration standard table.

In an embodiment of the present invention, the calibration standard table is generated using one or more predetermined proteins. The proteins are chemically or enzymatically treated to produce a set of characteristic polypeptide cleavage products. The polypeptide mixture(s) are analyzed by LC/MS to generate an inventory of the polypeptide masses and their corresponding signal responses. The LC/MS analysis is conducted with one or more known absolute quantities of the one or more calibration standard protein(s). The signal responses of the top N most efficiently ionizing polypeptides are selected from each calibration protein and the average signal response is incorporated into the calibration table. Using more calibration standard proteins over which to calculate peptide ionization sums or averages reduces statistical error.

In one embodiment, the present invention is a method for absolute quantitation of proteins in a sample. The method of the embodiment includes digesting the sample to obtain peptides associated with the proteins in the sample and analyzing the digestion products using an LC/MS apparatus to obtain an inventory of corresponding peptide masses along with their observed signal response for a particular protein. Further, the method of the embodiment includes determining the N most efficiently ionizing peptides observed from the LC/MS analysis for the particular protein and calculating the sum or average signal response for the N most efficiently ionizing polypeptides. In addition, the method of the embodiment includes comparing the calculated sum or average signal response to a calibration standard and determining an absolute quantity of the particular protein present in the sample based on the comparison.

In another embodiment, the present invention is a system for absolute quantitation of proteins in a sample. The system includes a mass spectrometer to generate an inventory of polypeptide masses along with their corresponding signal response to a particular protein in the sample and a computer. The computer includes a memory for storing a calibration standard table having entries for one or more proteins, each entry having a quantity of protein and the average signal response for the N most intense polypeptides to that protein. Further, the computer includes software executing thereon for enabling the computer to obtain ionization data from the mass spectrometer corresponding to peptides of the particular protein, analyze the obtained peptide ionization data, calculate one of the sum and average of the top N highest observed intensities, and determine an absolute quantity of the particular protein present in the sample by comparing the calculated sum or average to one or more entries in the calibration standard table.

BRIEF DESCRIPTION OF THE DRAWINGS

FIG. 16 is a table showing the top 3 most intense peptide signal responses each of the proteins in FIG. 1-6 for each amount of the protein tested.

DETAILED DESCRIPTION OF THE INVENTION

Figure 1:
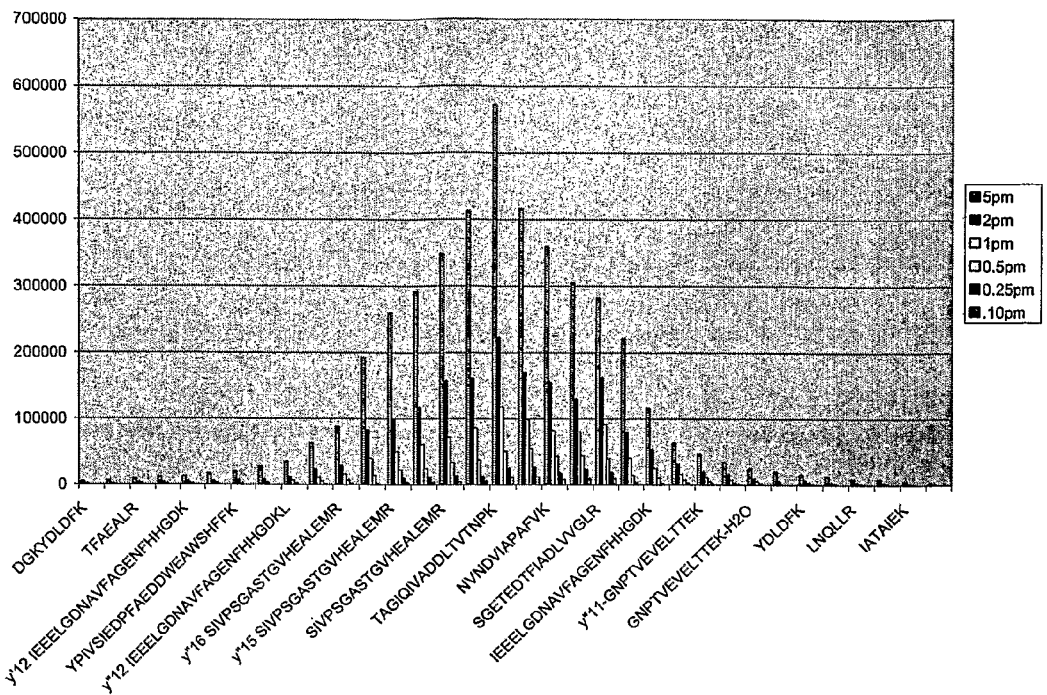
FIG. 1 is a bar plot showing the signal responses of peptides from varying quantities of yeast enolase.

Proteins are made of a linear sequence of amino acids that together produce a large, single polypeptide. Typically, during protein quantitation studies, the original protein molecules are chemically or enzymatically degraded into smaller cleavage peptides (e.g., tryptic peptides). For example, digestion using the enzyme trypsin breaks proteins into tryptic peptides by cutting the protein on the C-terminal side of the amino acids lysine and arginine.

Although the resulting peptides can be analyzed using a mass spectrometer, in general, because different peptides have different ionization efficiencies the signal response of the constituent peptides are not the same for any particular protein. That is, some peptides are more receptive to protonation/ionization than others. However, for any given protein the signal response of the tryptic peptides can be ordered to exhibit a Gaussian distribution.

As a result, the relative abundance of a protein can be determined by comparing the signal responses of peptides within a particular protein.

The inventors of the present invention discovered that from a serial dilution of equimolar levels of unrelated proteins, the average response from the N most efficiently ionizing peptides of a protein is similar across all proteins, where N is an integer. Other than the number of polypeptides produced from the enzymatic digestion there appears to be no effect regarding the size of the originating protein, the average signal response of the top N ionizing peptides from each protein is similar regardless of the intact proteins molecular weight to within +/−20%.

Using this knowledge, the inventors of the present invention have developed a system and method for absolute quantitation of proteins in a sample. According to embodiments of the present invention, the top N peptide signal responses for a particular protein are averaged. Assuming an equimolar amount of the protein, the average should be the same (to within some error) for all proteins. Consequently, the average can be compared to a pre-determined calibration standard average (that corresponds to an amount of peptide) to determine the absolute quantity of the protein of interest.

As an example of the foregoing, five common proteins were studied: hemoglobin from a cow (14,000 molecular weight); alcohol dehydrgenase from yeast (25,000 molecular weight); enolase from yeast (50,000 molecular weight); serum albumin from a cow (70,000 molecular weight); and glycogen phosphorylase (97,000 molecular weight). These proteins were analyzed at a level high enough to obtain substantially all of the peptides to the proteins.

Figure 2:
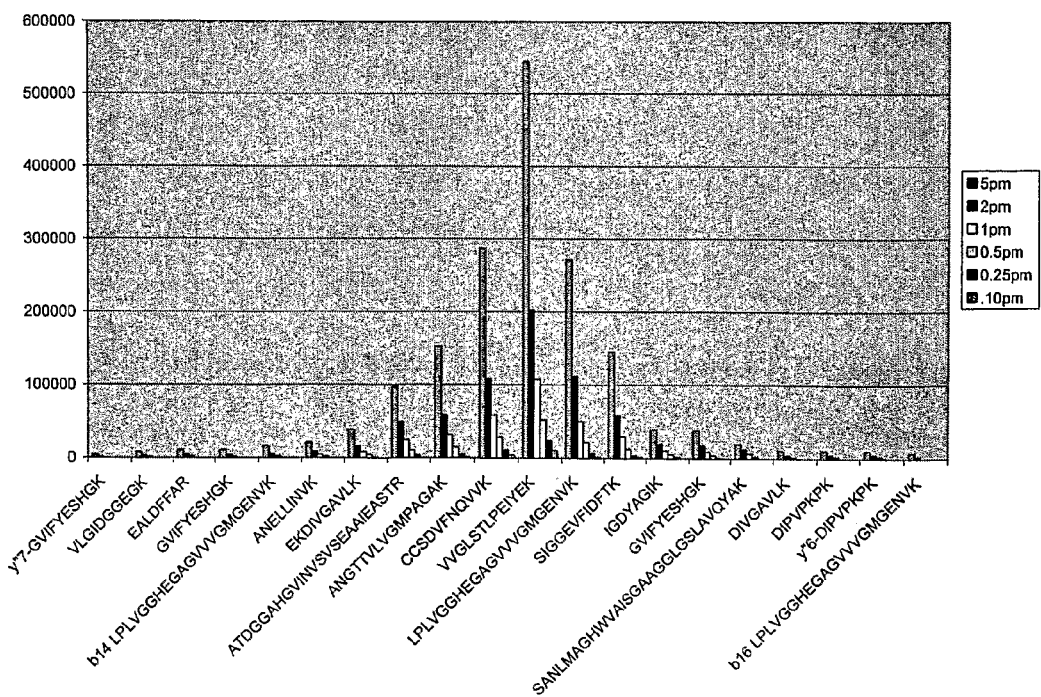
FIG. 2 is a bar plot showing the signal responses of peptides from varying quantities of yeast alcohol dehydrogenase.
Figure 3:
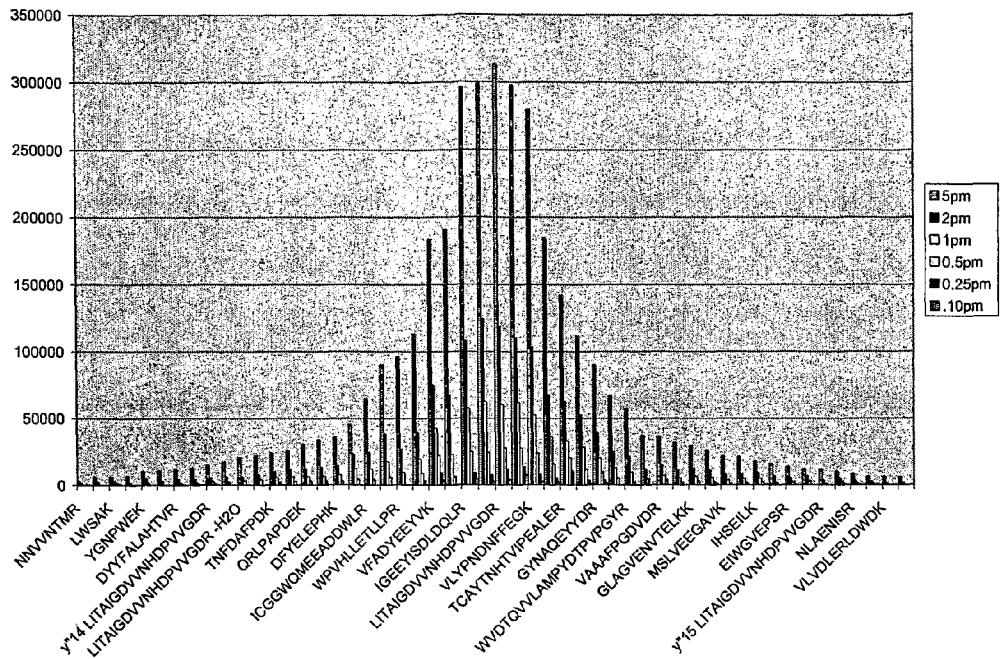
FIG. 3 is a bar plot showing the signal responses of peptides from varying quantities of rabbit glycogen phosphorylase.
Figure 4:
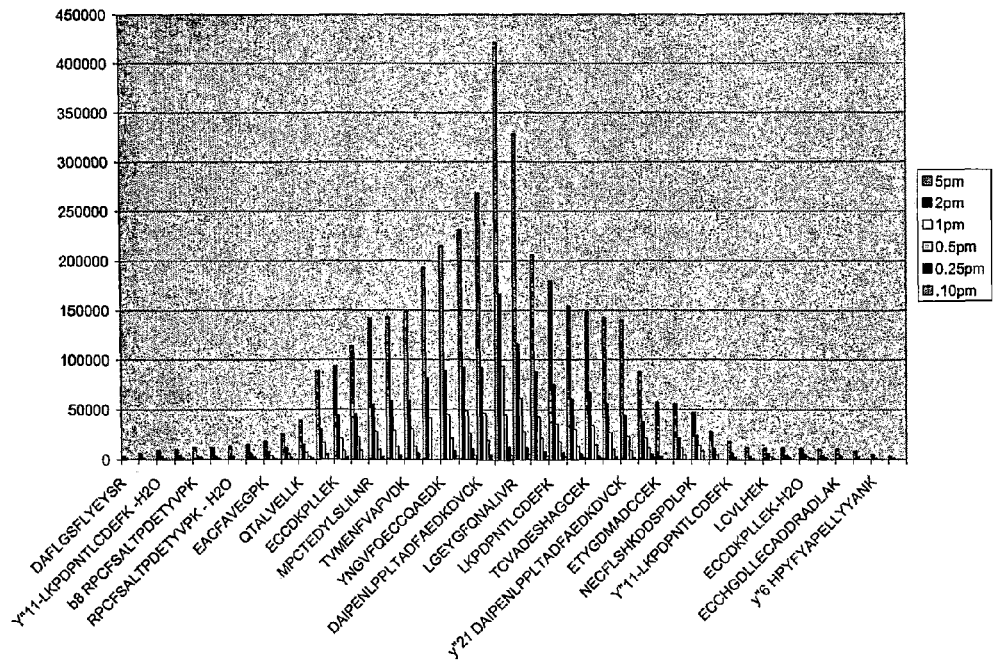
FIG. 4 is a bar plot showing the signal responses of peptides from varying quantities of bovine serum albumin.
Figure 5:
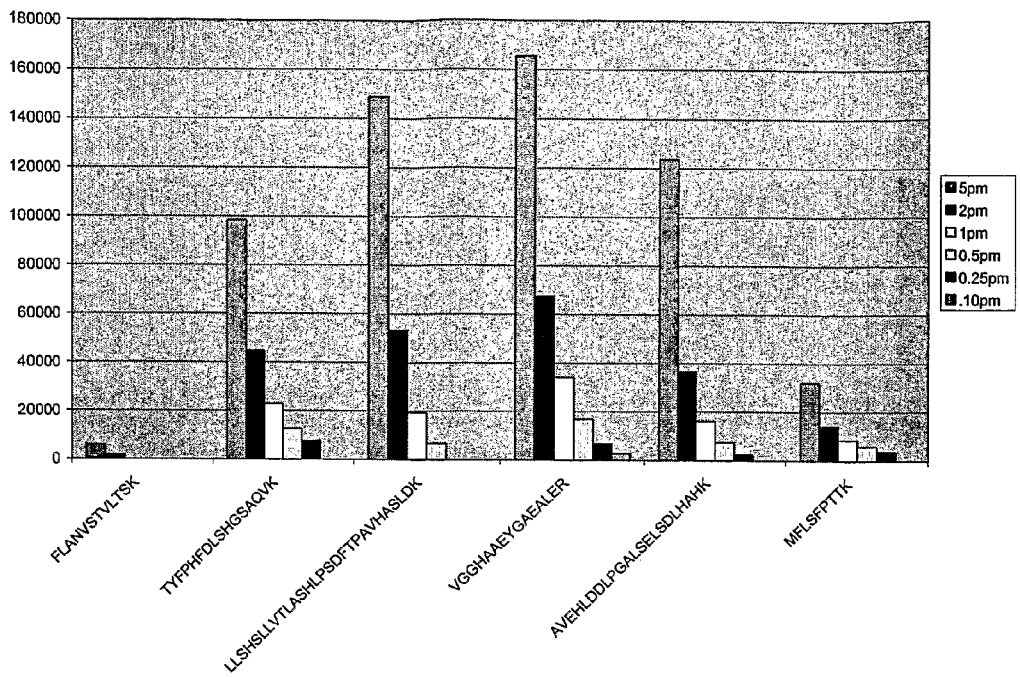
FIG. 5 is a bar plot showing the signal responses of peptides from varying quantities of bovine hemoglobin (alpha chain).
Figure 6:
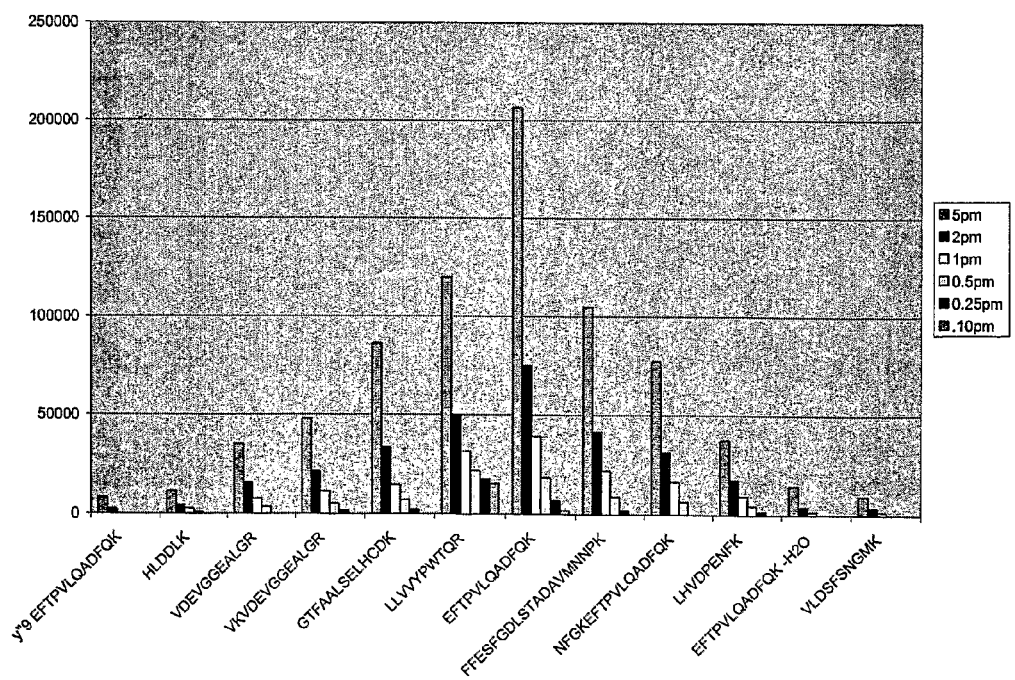
FIG. 6 is a bar plot showing the signal responses of peptides from varying quantities of bovine hemoglobin (beta chain).
Figure 7:
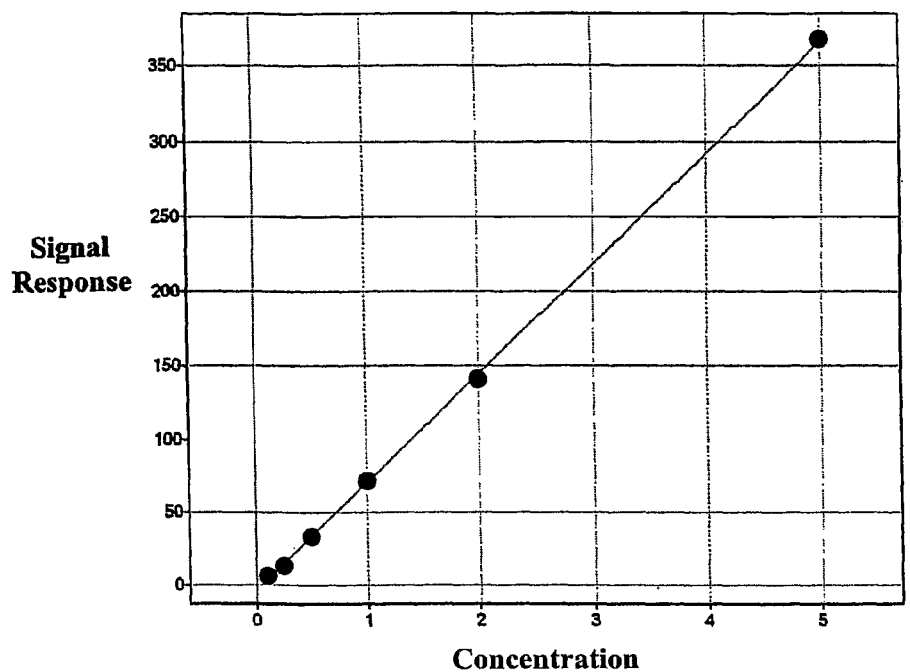
FIG. 7 is a plot of the average of the top 3 most intense peptide signal responses yeast enolase for the quantities illustrated in FIG. 1.
Figure 8:
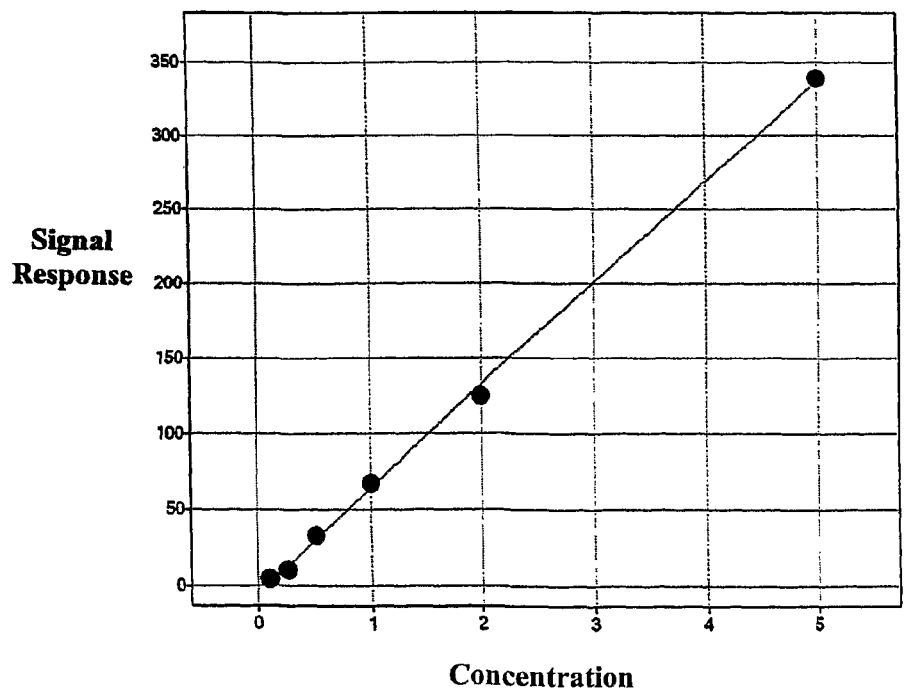
FIG. 8 is a plot of the average of the top 3 most intense peptide signal responses yeast alcohol dehydrogenase for the quantities illustrated in FIG. 2.
Figure 9:
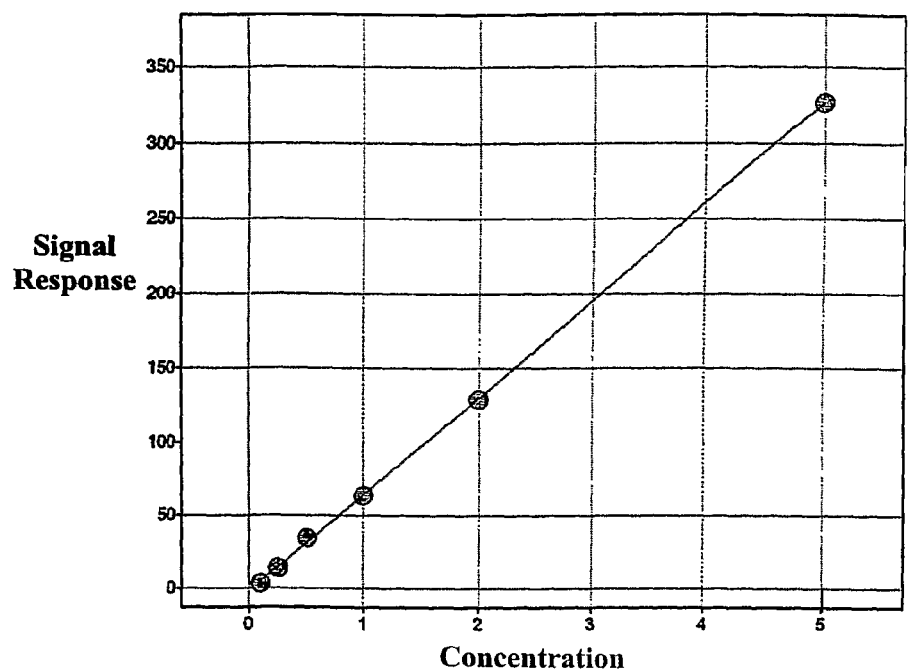
FIG. 9 is a plot of the average of the top 3 most intense peptide signal responses rabbit glycogen phosphorylase for the quantities illustrated in FIG. 3.
Figure 10:
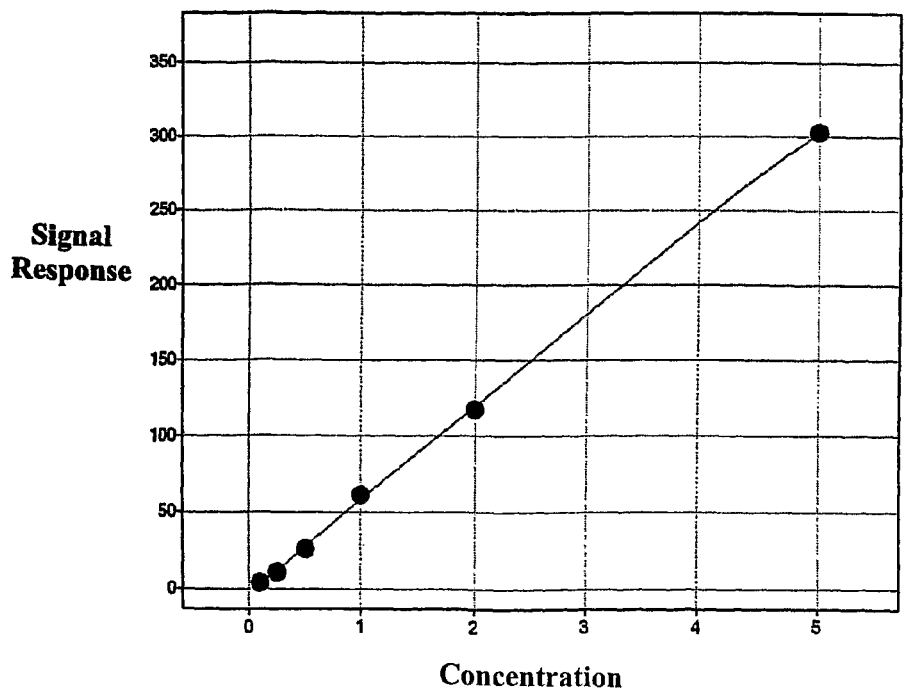
FIG. 10 is a plot of the average of the top 3 most intense peptide signal responses bovine serum albumin for the quantities illustrated in FIG. 4.
Figure 11:
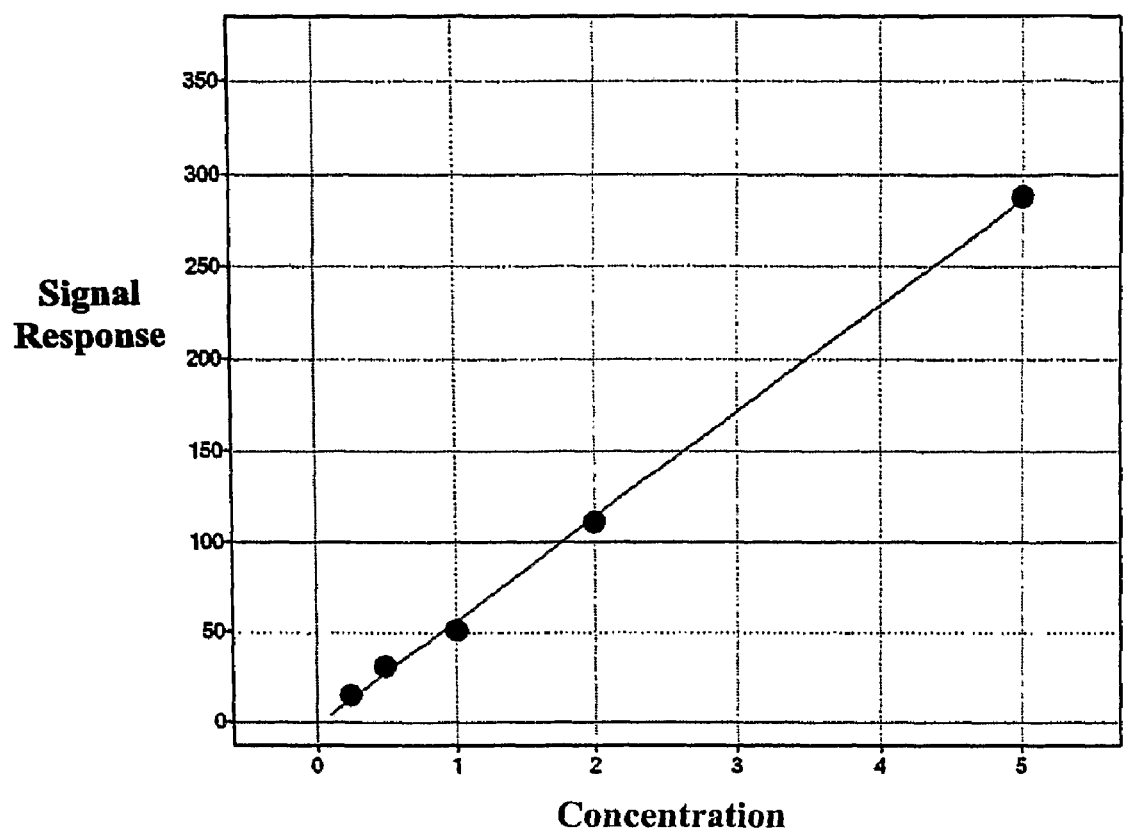
FIG. 11 is a plot of the average of the top 3 most intense peptide signal responses bovine hemoglobin (alpha and beta chains) for the quantities illustrated in FIGS. 5 and 6.

FIGS. 1-6 are bar plots of signal response (counts) for varying concentrations of each of the proteins analyzed. The x-axis of each of FIGS. 1-6 corresponds to the peptides in the protein (represented by their amino acid sequence). The y-axis of each of FIGS. 1-6 is the observed ionization signal response from the LC/MS analysis of the peptide mixture. Specifically, these varying concentrations are 5 pmol, 2 pmol, 1 pmol, 0.5 pmol, 0.25 pmol and 0.10 pmol. Specifically, FIG. 1 is a bar plot of the characterized peptides from yeast enolase (eno) digested using trypsin; FIG. 2 is a bar plot of the characterized peptides from yeast alcohol dehydrogenase (adh) digested using trypsin; FIG. 3 is a bar plot of the characterized peptides from rabbit glycogen phosphorylase (gp) digested using trypsin; FIG. 4 is a bar plot of the characterized peptides from bovin serum albumin (bs) digested using trypsin; FIG. 5 is a bar plot of the characterized peptides from bovine hemoglobin (alpha chain) (ha) digested using trypsin; and FIG. 6 is a bar plot of the characterized peptides from bovine hemoglobin (beta chain) (hb) digested using trypsin.

As seen in FIGS. 1-6, the signal responses associated with peptides for a particular protein can be arranged to exhibit a Gaussian distribution. This distribution suggests that broad categories of ionization efficiency can be established for the peptides of a particular protein—those that ionize well, those that ionize moderately, and those that ionize poorly. The ionization efficiency is directly related to the observed signal response. Ionization efficiency further appears to be a function of the presence of certain amino acids or sequences of amino acids. That is, certain amino acids or sequences of amino acids are more prevalent in peptides that ionize well than those that ionize less well.

Figure 17:
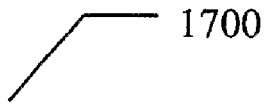
FIG. 17 is a table that tabulates the sum of the signal responses for each of the proteins in the table of FIG. 16.
Figure 18:
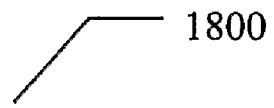
FIG. 18 is a table that tabulates the average of signal responses for each of the proteins in the table of FIG. 16.

FIG. 16 is a table 1600 showing the top 3 (i.e., N=3 in this example) peptide signal responses for each of the proteins in FIG. 1-6 for each concentration of the protein tested. FIGS. 17 and 18 are tables 1700 and 1800 that tabulate the sums and averages, respectively, for each of the proteins in table 1600. In Tables 1700 and 1800, the signal response values of ha and hb are added together for the sum and average signal responses because hemoglobin contains equal amounts of ha and hb. As can be seen, although the proteins are from different organisms and have different molecular weights, the average signal response of the top 3 ionizing peptides are virtually identical.

Figure 12:
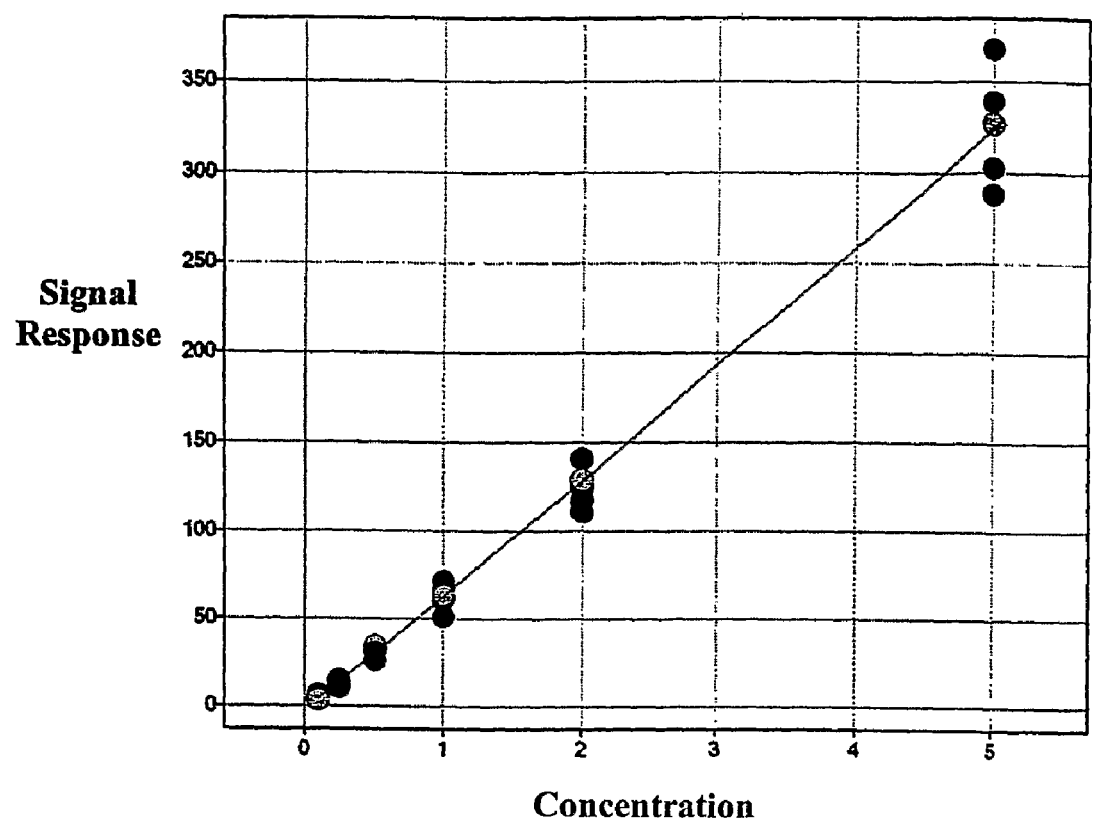
FIG. 12 is a composite plot of the signal responses shown in FIGS. 7 to 11.
Figure 13:
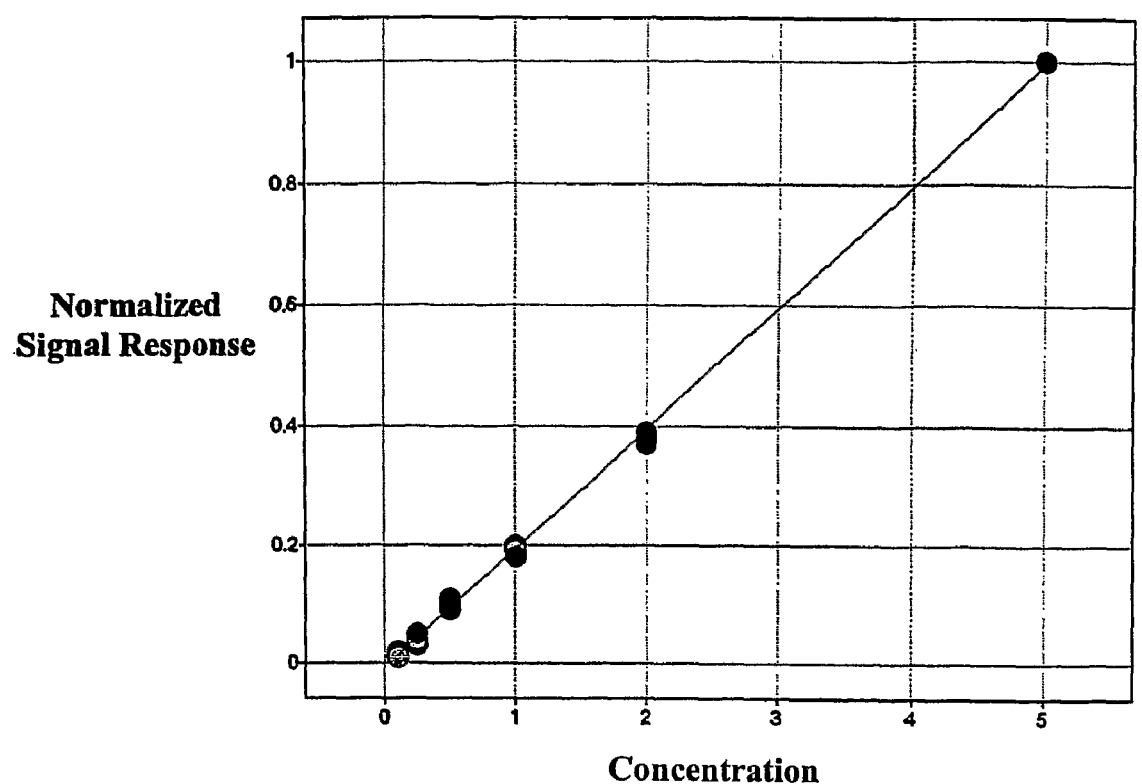
FIG. 13 is a composite normalized plot of the signal responses shown in FIG. 7 to 11.

FIGS. 7-11 are plots of the average signal response for the 3 most efficiently ionizing peptides for each of the proteins of FIGS. 1-6 as a function of the protein concentration. FIG. 12 is a composite plot of FIGS. 7-11. FIG. 13 is a composite normalized plot of FIG. 7-11. It is observed that the response is virtually linear. FIG. 13, moreover, demonstrates that the normalized responses are virtually identical independent of protein. Both of these characteristics support the conclusion that absolute quantity of a protein can be reliably determined using signal responses associated with the top N most efficiently ionizing peptides for a chosen one or more calibration standard proteins.

Thus, tables 1700 and 1800 provide a characteristic mole response for any peptide. For example, albumin can be selected as a calibration standard. Using mass spectrometry analysis of another protein, for example, enolase, the N (for example, 3) most efficiently ionizing peptides can be identified. Then the amount of the enolase that is present can be determined by comparing the signal response of the N most efficiently ionizing peptides to the albumin standard.

As another example, where N is 3, if the sum of the N highest ionizing peptides is on the order of 900,000 thousand counts from the MS analysis, then from table 1700, it is estimated that 5 picomole (pmol) of enolase is present. Similarly, if the average of the N most efficiently ionizing peptides is on the order of 300,000 counts, then from table 1800, the amount of enolase present is determined to be 5 pmol. Had the number of counts for the N most efficiently ionizing peptides of enolase been on the order of 100,000 counts (33,333 counts average), then the estimate from table 1700 or table 1800 for the amount of enolase present would have been 0.5 pmol. From tables 1700 and 1800, it can be seen that there are approximately 180,000 counts (60,000 counts average)/pmol of a particular protein present based on the N most efficiently ionizing peptides. In general, for a particular count, an estimate of the amount of protein present is given as follows by equation (1) if sums are used, and equation (2) if averages are used.

$$Q = \frac{\text{Observed Sum}}{\text{Sum in Table 1}} * \text{Corresponding concentration in Table 2} \quad (1)$$

$$Q = \frac{\text{Observed Avg}}{\text{Avg in Table 1}} * \text{Corresponding concentration in Table 3} \quad (2)$$

For example, if the average intensity signal responses of the N most efficiently ionizing peptides for a particular protein resulted in an average count of 650,000 counts, then using Equation 2 and Table 1800, an estimate for the absolute quantity of the protein is given by $$\frac{650,000}{324,800} * 5 \text{ pmol} = 10 \text{ pmol}.$$

the value 324,800 is the calibration standard average data value corresponding to 5 pmol from Table 1800. Likewise, using the 0.50 pmol concentration results in $$\frac{650,000}{31,800} * 0.5 \text{ pmol} = 10.2 \text{ pmol}.$$

Using a unimolar calibration standard value eliminates the need for the multiplication because the corresponding concentration is unity, i.e., 1. For example, using the 1.00 pmol value from Table 1800 yields $$\frac{650,000}{62,800} = 10.4 \text{ pmol}.$$

These values are within an acceptable error of one another.

Alternatively, well-known interpolation techniques (such as, for example, straight line, quadratic, polynomial, cubic spline) can be used to determine the molar concentration corresponding to a particular count.

The accuracy of these estimates can be provided by statistical analysis. Well known statistical analyses can be performed to provide confidence levels for the estimates. For example, tables 1700 and 1800 demonstrate that the coefficient of variation for the counts for any of the concentrations is within 20 percent. This is an acceptable range.

Figure 14:
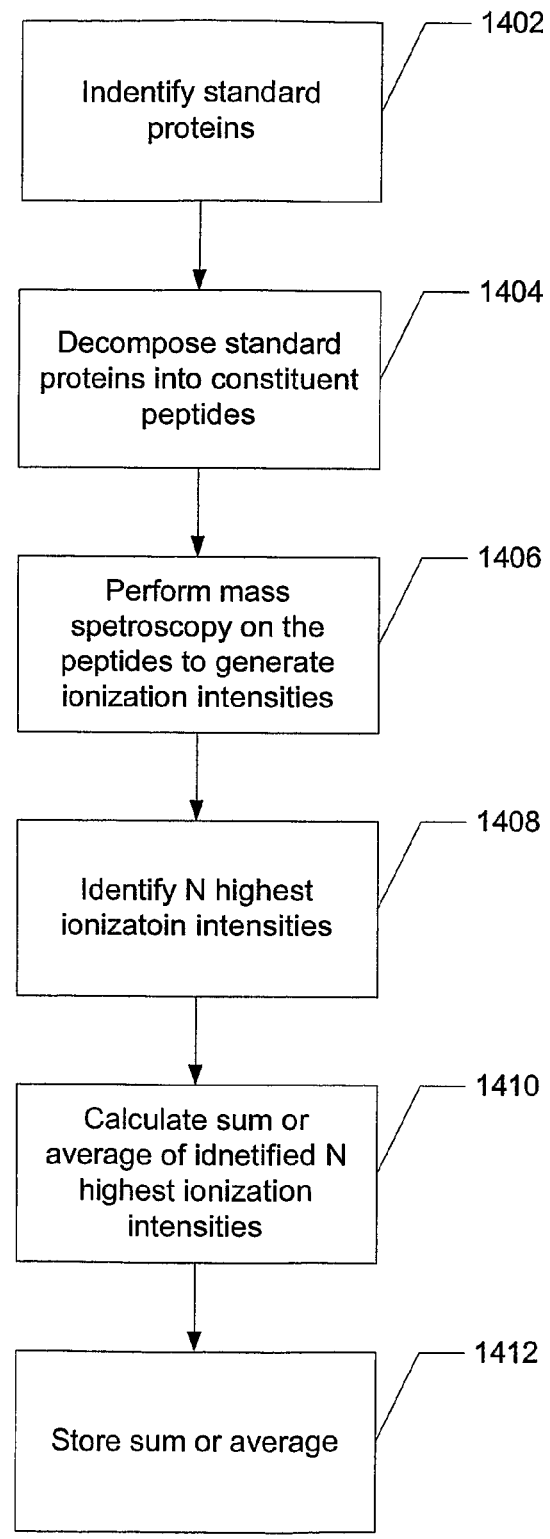
FIG. 14 is a flow chart for a method for generating a calibration standard table according to an embodiment of the present invention.

FIG. 14 is a flow chart for a method for generating a calibration standard table such as Tables 1700 and 1800 according to an embodiment of the present invention. In step 1402, one or more calibration standard proteins to be used for a calibration standard are identified. In step 1404, a known amount (in pmols) of each identified calibration standard protein is decomposed to generate its constituent peptides. For example, such decomposition can be digestion using the enzyme trypsin. The known amount can also be obtained using prepared digests such as the MassPREP™ peptide digestion standards (available for proteins such as Phophrylase b, Yeast Enolase, Bovine Hemoglobin, Yeast Alcohol Dehydrogenase and Bovine Serum Albumin) available from Waters Corporation, Milford, Mass. In step 1406, mass spectroscopic analysis is performed on the decomposition result. In step 1408, the N most efficiently ionizing peptides are identified. In step 1410, the sum or average of the N most efficiently ionizing peptides is determined. In step 1412, the sum or average is stored, for example, in a table such as table 1700 or 1800 along with the corresponding amount of protein. This process can be repeated for varying concentrations of protein. In an embodiment of the present invention, the table also includes the sum or average over all of the proteins, that is, a composite sum or average, for each of the concentrations in the table.

This process is repeated for a number of different amounts of the protein to generate a calibration standard table such as Table 1700 or 1800. Although only one protein need be used for the calibration standard, averaging values for a plurality of selected calibration standard proteins is desirable to improve the statistics of the technique. The calibration standard table can also have only the average sum or average of averages corresponding to each calibration standard protein, as well as optionally a covariance of the average sum or average of averages.

Any number of peptides can be used as the set of N most efficiently ionizing peptides. Using fewer than 3 however, may result in insufficient statistics to be accurate. As described, averages or sums can be used to generate the calibration standards tables. Any one or more proteins can be used as the set of calibration standard proteins. Any one or more different amounts of protein can be used to generate the calibration standards tables. Using more proteins, provides estimates on the coefficient of variation to provide additional confidence in subsequent analysis.

Larger proteins having more peptides are likely to have more peptides showing higher ionizations as more peptides increase the likelihood of having amino acid sequences that result in higher ionization efficiency. Smaller proteins, which produce fewer tryptic peptides, are less likely to have many peptides with amino acid sequences indicative of high ionization efficiency. Consequently, N is likely to be able to be set higher when larger proteins are being analyzed.

Storage of table 1700 precludes the need for regenerating the calibration standard table for each experiment. Moreover, the calibration standard table can be published or otherwise made available for others to use. For example, the table can be published in a journal or distributed by disk to interested users. Further, the table can be published on an Internet website, wherein distribution can be facilitated by a version of the table or tables that can be downloaded from the website. Numerous other methods for distributing such a calibration standard table would be well-known to those having skill in the art. Publication in this manner can be particularly advantageous wherein a particular user community agrees on one or more proteins to be used as the calibration standard.

The calibration standard table also acts to provide a calibration for a particular instrument. That is, the calibration determines, for a specific instrument, the number of counts observed per mole for a given protein. This value may vary from instrument to instrument. However, once this value is determined through calibration, it is applicable to the absolute quantitation of all proteins generated from the particular instruments(s).

Figure 15:
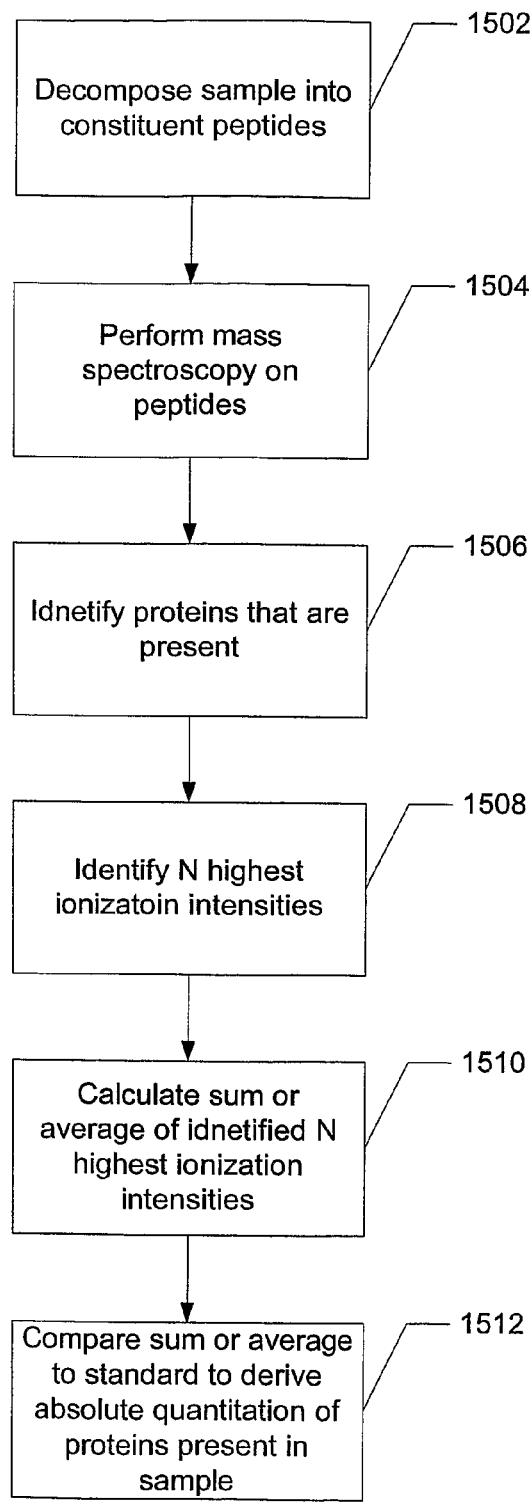
FIG. 15 is a flow chart for a method for using a calibration standard table generated according to an embodiment of the present invention.

FIG. 15 is a flow chart for a method for using a calibration standard table generated according to an embodiment of the present invention. In step 1502, a sample containing a protein or complex mixture of proteins is decomposed into its constituent peptides and run through the LCMS to collect the data. As above, the decomposition can be digestion using the enzyme Trypsin. In step 1504, mass spectroscopic analysis is performed on the decomposition result. In step 1506, proteins are identified. In step 1508, the N most efficiently ionizing peptides are identified for each protein identified in step 1506. In step 1510, the sum or average (depending on the calibration standard table used) of the N most efficiently ionizing peptides is determined for each of the proteins. In step 1512, the sum (or average) is compared to the calibration standard table. If the sum (or average) is present, then the corresponding amount of protein is used as the number.

If the sum or average is not present, then the comparison includes calculating the absolute amount of protein based on the comparison. Such calculation can include applying the conversion described above in equations (1) or (2), or using other well-known interpolation techniques (including, for example, straight line, quadratic, polynomial, cubic spline) can be used to estimate the molar amount of the protein based on the counts. Alternatively, if the calibration standard table includes count data corresponding to a single mole of protein, then the calculation can be dividing the observed count by the count in the calibration standard table corresponding to one mole to obtain an estimate of the molar amount of a particular protein present.

As with generating the standard table, any number of peptides can be used as the set of N most efficiently ionizing peptides. Using fewer than 3 however, may result in insufficient statistics to be accurate.

In either the case of generating the table or using the table, if averages are used, then N can be different for different proteins. This may reduce coefficients of variation when using larger proteins, thereby increasing confidence in absolute quantitation estimates.

Figure 19:
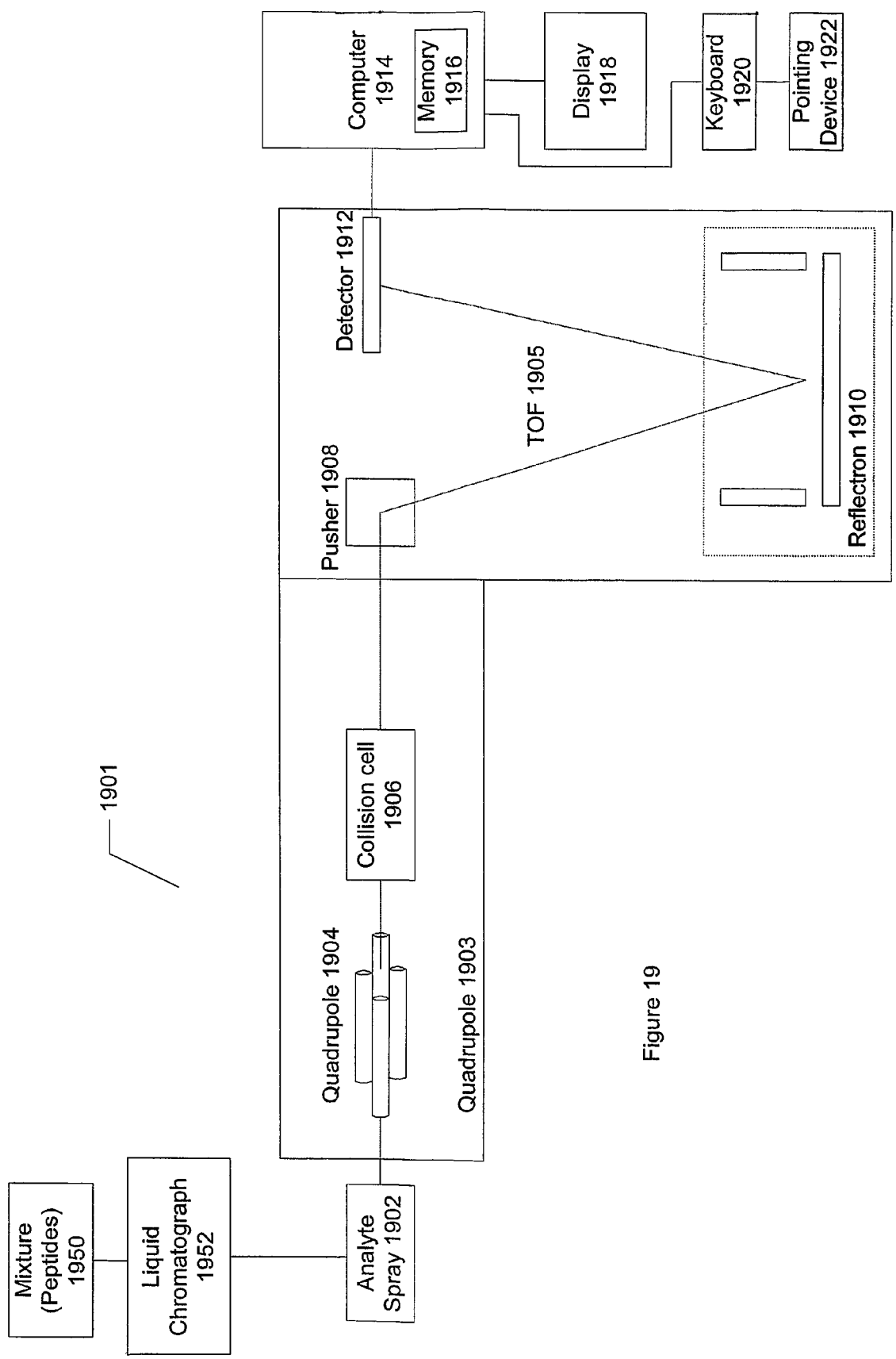
FIG. 19 is a schematic diagram of a system for absolute quantitation according to an embodiment of the present invention.

FIG. 19 is a schematic diagram of a system for absolute quantitation according to an embodiment of the present invention. The system includes a liquid chromatograph 1952 coupled to a mass spectrometer 1901. Mass spectrometer 1901 is coupled to a computer 1914. Liquid chromatograph 1952 can also be coupled to computer 1914. In the exemplary embodiment of the present invention illustrated in FIG. 19, mass spectrometer 1901 is a Q-TOF instrument, available from Waters Corp. (Milford, Mass.). In the exemplary embodiment of the present invention illustrated in FIG. 19, liquid chromatograph 1952 is a nanoACQUITY™ UPLC System or Water CapLC, available from Waters Corp. (Milford, Mass.).

In operation, a protein mixture is either chemically or enzymatically degraded into peptide components, thereby forming a peptide mixture 1950. Peptide mixture 1950 is separated in LC 1952. The separation components are introduced to mass spectrometer 1901. One method for such introduction is using electrospray ionization to produce an analyte spray 1902.

Analyte spray 1902 is introduced to a quadrupole section 1903 of mass spectrometer 1901. In the quadrupole section, quadrupole 1904 is tuned to select a particular ion for subsequent analysis in time-of-flight section 1905 of mass spectrometer 1901. The selected ion is fragmented in collision cell 1906. The fragments are introduced into time-of-flight section 1905. In time-of-flight section 1905, a pusher 1908 pushes the fragments toward a reflectron 1910. Reflectron 1910 reflects the ions to a detector 1912. Detector 1912 detects ion intensities and forwards them to a computer 1914 for subsequent analysis. Computer 1914 executes software to analyze the fragments in accordance with embodiments of the present invention described above. Computer 1914 can be any computer and computer apparatus that can be configured to implement the present invention as described herein. Computer 1914 also includes memory 1916 for storing a calibration standard tables such as calibration standard table 1700. Memory 1916 can be any memory, internal or external, that can store table 1700 including for example, RAM, ROM, PROM, EPROM, EEPROM, magnetic disk, optical disk, or CD-ROM. A screen or display 1918 is coupled to computer 1914 for displaying information to a user. A keyboard 1920 is also coupled to computer 1914 to allow a user to enter data. Keyboard 1920 can also have a mouse or other pointing device coupled thereto to assist the user in operating computer 1914 in a well known manner. Computers such as computer 1914 and its memory 1916 as well as computer peripherals such as display 1918, keyboard 1920 and pointing device 1922 are well known to those skilled in the art, and need not be described further.

The present invention provides not only a system and method for determining absolute quantity of proteins in a sample, but also a method for validating the quantitation. For example, assume an absolute quantitation for the protein glycogen phosphorylase was obtained using and embodiment of the present invention. Assume further that only 5 high ionization efficiency peptides were observed. FIG. 3 illustrates that glycogen phosphorylase should have 8 high ionization efficiency peptides. Consequently, observation of only 5 such peptides indicates a possible error in the experiment.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for absolute quantitation of proteins in a sample, comprising:
   digesting the sample to obtain peptides associated with the proteins in the sample;
   analyzing the digestion products using a liquid chromatography/mass spectrometry apparatus to obtain peptide ionization intensities for a particular protein;
   determining an N highest peptide ionization intensities observed for the particular protein;
   calculating one of a sum intensity of the N highest peptide ionization intensities observed and an average intensity of the N highest peptide ionization intensities observed;
   comparing the calculated sum intensity or the average intensity to a calibration standard; and
   determining an absolute quantity of the particular protein present in the sample based on said comparing.

2. The method recited in claim 1, wherein N is greater or equal to three (3).

3. The method recited in claim 1, further comprising generating a calibration standard.

4. The method recited in claim 3, further comprising:
   (a) obtaining a known, quantity of a predetermined protein in a calibration standard mixture;
   (b) digesting the calibration standard mixture to obtain peptides associated with the protein;
   (c) analyzing the peptides to determine peptide ionization intensities corresponding to the peptides;
   (d) selecting an N highest peptide intensities;
   (e) calculating one of the sum and the average of the selected N highest peptide intensities; and
   (f) storing the calculated sum or average in a table for later use as a calibration standard.

5. The method recited in claim 4, wherein N is greater or equal to three (3).

6. The method recited in claim 4, comprising repeating step (a)-(f) for one or more additional predetermined proteins.

7. The method recited in claim 4, comprising repeating step (a)-(f) for one or more known concentrations of the predetermined protein.

8. The method recited in claim 1, further comprising identifying the particular protein.

9. The method recited in claim 1, further comprising calculating the amount of the particular protein using interpolation.

10. The method recited in claim 1, further comprising converting the observed amount based on quantities in the calibration standard.

11. A method for absolute quantitation of proteins in a sample, comprising:
    creating a calibration standard table having entries for one or more proteins, each entry having an amount of protein and one of a corresponding sum or average signal response for that protein;
    obtaining peptides corresponding to a protein in the sample;
    analyzing the obtained peptides using a mass spectrometer to obtain ionization intensities corresponding to the peptides;

calculating one of a sum intensity of N highest peptide ionization intensities obtained in said analyzing and an average intensity of the N highest peptide ionization intensities obtained in said analyzing; and determining an, absolute quantity of the particular protein present in the sample by comparing the calculated sum intensity or the average intensity to one or more entries in the calibration standard table.

12. The method recited in claim 11, wherein N is greater or equal to three (3).

13. The method recited in claim 11, wherein creating the calibration standard table, comprises:
  (a) obtaining a known quantity of a predetermined protein in a calibration standard mixture;
  (b) digesting the calibration standard mixture to obtain peptides associated with the protein;
  (c) analyzing the peptides to determine ionization intensities corresponding to the peptides;
  (d) selecting an N highest ionizing intensities;
  (e) calculating one of the sum and the average of the selected N highest ionization intensities; and
  (f) storing the calculated sum or average in the calibration standard table.

14. The method recited in claim 13, wherein N is greater or equal to three (3).

15. The method recited in claim 13, comprising repeating step (a)-(f) for one or more additional predetermined proteins.

16. The method recited in claim 11, further comprising distributing the calibration standard table.

17. The method recited in claim 11, further comprising making the calibration standard table available for distribution on an Internet website.

18. A system for absolute quantitation of proteins in a sample, comprising:
  a mass spectrometer to generate ionization intensities for peptides corresponding to a particular protein in the sample; and
  a computer, comprising
    a memory for storing a calibration standard table having entries for one or more proteins, each entry having an amount of protein and one of a corresponding sum or average signal response for that protein; and
  a non-transitory computer readable medium including instructions stored thereon which, when executed, perform processing including:
    obtaining ionization data from the mass spectrometer corresponding to peptides of the particular protein;
    analyzing the obtained peptide ionization data;
    calculating one of a sum intensity of N highest peptide ionization intensities of the obtained peptide ionization data and average of the N highest peptide ionization intensities of the obtained peptide ionization data; and
    determining an absolute quantity of the particular protein present in the sample by comparing the calculated sum intensity or the average intensity to one or more entries in the calibration standard table.

19. The system recited in claim 18, further comprising a liquid chromatograph to separate a sample into constituent proteins for subsequent analysis.

20. The system recited in claim 18, wherein N is greater or equal to three (3).

* * * * *